(12) United States Patent
Zubok et al.

(10) Patent No.: US 8,425,609 B2
(45) Date of Patent: Apr. 23, 2013

(54) ARTIFICIAL INTERVERTEBRAL DISC HAVING A BORED SEMISPHERICAL BEARING WITH A COMPRESSION LOCKING POST AND RETAINING CAPS

(75) Inventors: Rafail Zubok, Midland Park, NJ (US); Michael W. Dudasik, Nutley, NJ (US); Joseph P. Errico, Green Brook, NJ (US)

(73) Assignee: SpineCore, Inc., Allendale, NJ (US)

( * ) Notice: Subject to any disclaimer, the term of this patent is extended or adjusted under 35 U.S.C. 154(b) by 624 days.

(21) Appl. No.: 12/154,475

(22) Filed: May 23, 2008

(65) Prior Publication Data
US 2008/0306594 A1    Dec. 11, 2008

Related U.S. Application Data

(63) Continuation of application No. 10/782,982, filed on Feb. 20, 2004, now Pat. No. 7,393,361.

(51) Int. Cl.
*A61F 2/44* (2006.01)

(52) U.S. Cl.
USPC .................................................. 623/17.16

(58) Field of Classification Search ..... 623/17.11–17.16
See application file for complete search history.

(56) References Cited

U.S. PATENT DOCUMENTS

| | | |
|---|---|---|
| 2,193,122 A | 3/1940 | Crabbs |
| 3,867,728 A | 2/1975 | Stubstad et al. |
| 4,309,777 A | 1/1982 | Patil |
| 4,566,466 A | 1/1986 | Ripple et al. |
| 4,605,417 A | 8/1986 | Fleischauer |
| 4,759,766 A | 7/1988 | Buettner-Janz et al. |
| 4,759,769 A | 7/1988 | Hedman et al. |
| 4,874,389 A * | 10/1989 | Downey ............... 623/17.16 |
| 4,932,969 A | 6/1990 | Frey et al. |
| 4,997,432 A | 3/1991 | Keller et al. |
| 5,034,254 A | 7/1991 | Cologna et al. |
| 5,236,460 A | 8/1993 | Barber |
| 5,258,031 A | 11/1993 | Salib et al. |
| 5,306,308 A | 4/1994 | Gross et al. |
| 5,314,477 A | 5/1994 | Marnay et al. |
| 5,370,697 A | 12/1994 | Baumgartner |
| 5,401,269 A | 3/1995 | Buttner-Janz et al. |
| 5,425,773 A | 6/1995 | Boyd et al. |
| 5,458,642 A | 10/1995 | Beer et al. |
| 5,507,816 A | 4/1996 | Bullivant et al. |

(Continued)

FOREIGN PATENT DOCUMENTS

WO    WO-97/10776 A2    3/1997

*Primary Examiner* — Thomas J Sweet
*Assistant Examiner* — Cheryl Miller
(74) *Attorney, Agent, or Firm* — Lerner, David, Littenberg, Krumholz & Mentlik, LLP

(57) ABSTRACT

An artificial intervertebral disc having a pair of opposing baseplates, for seating against opposing vertebral bone surfaces, uses a semispherical, bored bearing that is secured to the baseplates with compression locking posts and one or more retaining caps. The compression locking posts extend through the bearing bore and baseplate apertures such that the bearing is between the baseplates' inwardly facing surfaces. Retaining caps are attached to the compression locking posts, securing the baseplates to the bearing. Bearing surfaces on the inwardly facing side of each baseplate allow each baseplate to rotate relative to the bearing, however, rotation of each baseplate is limited by the interference of each baseplate and its respective retaining cap. Rotation of the baseplates about the longitudinal axis of the spine can be limited via a notch in the retaining caps and a groove in the baseplates, or vice versa.

25 Claims, 6 Drawing Sheets

U.S. PATENT DOCUMENTS

| | | | |
|---|---|---|---|
| 5,514,180 | A | 5/1996 | Heggeness et al. |
| 5,556,431 | A | 9/1996 | Buttner-Janz et al. |
| 5,562,738 | A | 10/1996 | Boyd et al. |
| 5,674,296 | A | 10/1997 | Bryan et al. |
| 5,676,701 | A | 10/1997 | Yuan et al. |
| 5,676,702 | A | 10/1997 | Ratron et al. |
| 5,683,464 | A | 11/1997 | Wagner et al. |
| 5,683,465 | A | 11/1997 | Shinn et al. |
| 5,755,796 | A | 5/1998 | Ibo et al. |
| 5,782,830 | A | 7/1998 | Farris |
| 5,782,832 | A | 7/1998 | Larsen et al. |
| 5,827,328 | A | 10/1998 | Buttermann |
| 5,865,846 | A | 2/1999 | Bryan et al. |
| 5,888,226 | A | 3/1999 | Rogozinski |
| 5,893,889 | A | 4/1999 | Harrington |
| 5,895,428 | A | 4/1999 | Berry |
| 5,899,941 | A | 5/1999 | Nishijima et al. |
| 5,989,291 | A | 11/1999 | Ralph et al. |
| 6,001,030 | A | 12/1999 | Delaney |
| 6,019,792 | A | 2/2000 | Cauthen |
| 6,039,763 | A | 3/2000 | Shelokov |
| 6,063,121 | A | 5/2000 | Xavier et al. |
| 6,066,174 | A | 5/2000 | Farris |
| 6,113,637 | A | 9/2000 | Gill et al. |
| 6,136,031 | A | 10/2000 | Middleton |
| 6,146,421 | A | 11/2000 | Gordon et al. |
| 6,156,067 | A | 12/2000 | Bryan et al. |
| 6,159,215 | A | 12/2000 | Urbahns et al. |
| 6,174,311 | B1 | 1/2001 | Branch et al. |
| 6,179,874 | B1 | 1/2001 | Cauthen |
| 6,228,118 | B1 | 5/2001 | Gordon |
| 6,280,458 | B1 | 8/2001 | Boche et al. |
| 6,319,257 | B1 | 11/2001 | Carignan et al. |
| 6,368,350 | B1 | 4/2002 | Erickson et al. |
| 6,375,682 | B1 | 4/2002 | Fleischmann et al. |
| 6,416,551 | B1 | 7/2002 | Keller |
| 6,428,544 | B1 | 8/2002 | Ralph et al. |
| 6,436,102 | B1 | 8/2002 | Ralph et al. |
| 6,471,725 | B1 | 10/2002 | Ralph et al. |
| 6,478,796 | B2 | 11/2002 | Zucherman et al. |
| 6,478,800 | B1 | 11/2002 | Fraser et al. |
| 6,478,801 | B1 | 11/2002 | Ralph et al. |
| 6,517,580 | B1 | 2/2003 | Ramadan et al. |
| 6,527,804 | B1 | 3/2003 | Gauchet et al. |
| 6,554,864 | B2 | 4/2003 | Ralph et al. |
| 6,579,320 | B1 | 6/2003 | Gauchet et al. |
| 6,582,466 | B1 | 6/2003 | Gauchet et al. |
| 6,582,468 | B1 | 6/2003 | Gauchet et al. |
| 6,592,624 | B1 | 7/2003 | Fraser et al. |
| 6,607,559 | B2 | 8/2003 | Ralph et al. |
| 6,610,092 | B2 | 8/2003 | Ralph et al. |
| 6,623,525 | B2 | 9/2003 | Ralph et al. |
| 6,645,249 | B2 | 11/2003 | Ralph et al. |
| 6,669,732 | B2 | 12/2003 | Serhan et al. |
| 6,673,113 | B2 | 1/2004 | Ralph et al. |
| 6,682,562 | B1 | 1/2004 | Viart et al. |
| 6,692,495 | B1 | 2/2004 | Zacouto et al. |
| 6,706,068 | B2 | 3/2004 | Ferree |
| 6,709,458 | B2 * | 3/2004 | Michelson ................. 623/17.15 |
| 6,716,245 | B2 | 4/2004 | Pasquet et al. |
| 6,945,500 | B2 | 9/2005 | Wingo |
| 6,989,032 | B2 | 1/2006 | Errico et al. |
| 7,001,433 | B2 | 2/2006 | Songer et al. |
| 7,214,244 | B2 | 5/2007 | Zubok et al. |
| 7,393,361 | B2 * | 7/2008 | Zubok et al. ............... 623/17.15 |
| 7,604,664 | B2 * | 10/2009 | Ralph et al. ................. 623/17.14 |
| 2001/0007073 | A1 | 7/2001 | Zucherman et al. |
| 2001/0016773 | A1 | 8/2001 | Serhan et al. |
| 2001/0020170 | A1 | 9/2001 | Zucherman et al. |
| 2001/0039452 | A1 | 11/2001 | Zucherman et al. |
| 2002/0062131 | A1 | 5/2002 | Gallo |
| 2002/0082695 | A1 | 6/2002 | Neumann |
| 2002/0099377 | A1 | 7/2002 | Zucherman et al. |
| 2002/0111679 | A1 | 8/2002 | Zucherman et al. |
| 2002/0111681 | A1 | 8/2002 | Ralph et al. |
| 2002/0111682 | A1 | 8/2002 | Ralph et al. |
| 2002/0111684 | A1 | 8/2002 | Ralph et al. |
| 2002/0111685 | A1 | 8/2002 | Ralph et al. |
| 2002/0128714 | A1 | 9/2002 | Manasas et al. |
| 2002/0161375 | A1 | 10/2002 | Ralph et al. |
| 2003/0014057 | A1 | 1/2003 | Ralph et al. |
| 2003/0014109 | A1 | 1/2003 | Ralph et al. |
| 2003/0014110 | A1 | 1/2003 | Ralph et al. |
| 2003/0014112 | A1 | 1/2003 | Ralph et al. |
| 2003/0014113 | A1 | 1/2003 | Ralph et al. |
| 2003/0014114 | A1 | 1/2003 | Ralph et al. |
| 2003/0014115 | A1 | 1/2003 | Ralph et al. |
| 2003/0014116 | A1 | 1/2003 | Ralph et al. |
| 2003/0023245 | A1 | 1/2003 | Ralph et al. |
| 2003/0023309 | A1 | 1/2003 | Ralph et al. |
| 2003/0023310 | A1 | 1/2003 | Ralph et al. |
| 2003/0028197 | A1 | 2/2003 | Hanson et al. |
| 2003/0028249 | A1 | 2/2003 | Baccelli et al. |
| 2003/0028252 | A1 | 2/2003 | Ralph et al. |
| 2003/0040801 | A1 | 2/2003 | Ralph et al. |
| 2003/0055503 | A1 | 3/2003 | O'Neil |
| 2003/0060886 | A1 | 3/2003 | Van Hoeck et al. |
| 2003/0069586 | A1 | 4/2003 | Errico et al. |
| 2003/0069642 | A1 | 4/2003 | Ralph et al. |
| 2003/0074067 | A1 | 4/2003 | Errico et al. |
| 2003/0100951 | A1 | 5/2003 | Serhan et al. |
| 2003/0125748 | A1 | 7/2003 | Li et al. |
| 2003/0149438 | A1 | 8/2003 | Nichols et al. |
| 2003/0149482 | A1 | 8/2003 | Michelson |
| 2003/0187508 | A1 | 10/2003 | Cauthen |
| 2003/0191534 | A1 | 10/2003 | Viart et al. |
| 2003/0199981 | A1 | 10/2003 | Ferree |
| 2003/0204260 | A1 | 10/2003 | Ferree |
| 2003/0208271 | A1 | 11/2003 | Kuras |
| 2003/0225408 | A1 | 12/2003 | Nichols et al. |
| 2003/0229358 | A1 | 12/2003 | Errico et al. |
| 2003/0233097 | A1 | 12/2003 | Ferree |
| 2003/0233148 | A1 | 12/2003 | Ferree |
| 2004/0002759 | A1 | 1/2004 | Ferree |
| 2004/0002762 | A1 | 1/2004 | Hawkins |
| 2004/0010316 | A1 | 1/2004 | William et al. |
| 2004/0024406 | A1 | 2/2004 | Ralph et al. |
| 2004/0024407 | A1 | 2/2004 | Ralph et al. |
| 2004/0030387 | A1 | 2/2004 | Landry et al. |
| 2004/0030389 | A1 | 2/2004 | Ferree |
| 2004/0030390 | A1 | 2/2004 | Ferree |
| 2004/0034426 | A1 | 2/2004 | Errico et al. |
| 2004/0078079 | A1 | 4/2004 | Foley |
| 2004/0117021 | A1 * | 6/2004 | Biedermann et al. ...... 623/17.15 |
| 2004/0167626 | A1 * | 8/2004 | Geremakis et al. ........ 623/17.15 |
| 2005/0021146 | A1 * | 1/2005 | de Villiers et al. ......... 623/17.15 |
| 2005/0085910 | A1 * | 4/2005 | Sweeney .................... 623/17.11 |
| 2006/0259146 | A1 | 11/2006 | Navarro et al. |
| 2007/0299524 | A1 * | 12/2007 | Rivin ........................ 623/17.13 |
| 2010/0070042 | A1 * | 3/2010 | Bryan et al. ................ 623/17.16 |

* cited by examiner

ARTIFICIAL INTERVERTEBRAL DISC HAVING A BORED SEMISPHERICAL BEARING WITH A COMPRESSION LOCKING POST AND RETAINING CAPS

CROSS-REFERENCE TO RELATED APPLICATION

This application is a continuation of U.S. application Ser. No. 10/782,982, filed on Feb. 20, 2004 now U.S. Pat. No. 7,393,361, the disclosure of which is incorporated herein by reference.

BACKGROUND OF THE INVENTION

This invention relates generally to a device for implantation into an intervertebral space to simultaneously stabilize the adjacent vertebral bodies and permit proper anatomical motion at the segment. Specifically, the present invention relates to such a device having upper and lower baseplates that articulate about a central, bored semispherical bearing. The present invention maximizes the strength (i.e., compression and tension load capabilities) of such a device by allowing the semispherical bearing to have a larger diameter without increasing the height of the device.

The bones and connective tissue of an adult human spinal column consist of more than twenty discrete bones coupled sequentially to one another by a tri-joint complex, which consists of an anterior disc and two posterior facet joints, the anterior discs of adjacent bones being cushioned by cartilage spacers referred to as intervertebral discs. These more than twenty bones are anatomically categorized as being members of one of four classifications: cervical, thoracic, lumbar, or sacral. The cervical portion of the spine, which comprises the top of the spine up to the base of the skull, includes the first seven vertebrae. The intermediate twelve bones are the thoracic vertebrae, and connect to the lower spine comprising the five lumbar vertebrae. The base of the spine comprises the sacral bones (including the coccyx). The component bones of the cervical spine are generally smaller than those of the thoracic spine, which are in turn smaller than those of the lumbar region. The sacral region connects laterally to the pelvis.

The spinal column is highly complex in that it includes these more than twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. A variety of systems have been disclosed in the art that achieve immobilization and/or fusion of adjacent bones by implanting artificial assemblies in or on the spinal column. The region of the back that needs to be immobilized, as well as the individual variations in anatomy, determines the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 2-3, in which a side perspective view of an intervertebral body cage and an anterior perspective view of a post implantation spinal column are shown, respectively, a more complete description of these devices of the prior art is herein provided. These cages 1 generally comprise tubular metal body 2 having an external surface threading 3. They are inserted transverse to the axis of the spine 4, into preformed cylindrical holes at the junction of adjacent vertebral bodies (in FIG. 3 the pair of cages 1 are inserted between the fifth lumbar vertebra (L5) and the top of the sacrum (S1)). Two cages 1 are generally inserted side by side with the external surface threading 3 tapping into the lower surface of the vertebral bone above (L5), and the upper surface of the vertebral bone (S1) below. The cages 1 include holes 5 through which the adjacent bones are to grow. Additional materials, for example autogenous bone graft materials, may be inserted into the hollow interior 6 of the cage 1 to incite or accelerate the growth of the bone into the cage. End caps (not shown) are often utilized to hold the bone graft material within the cage 1.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which mimics the biomechanical action of the natural disc cartilage, thereby permitting continued normal motion and stress distribution.

It is, therefore, an object of the invention to provide an intervertebral spacer that stabilizes the spine without promoting a bone fusion across the intervertebral space.

It is further an object of the invention to provide an implant device that stabilizes the spine while still permitting normal motion.

It is further an object of the invention to provide a device for implantation into the intervertebral space that does not promote the abnormal distribution of biomechanical stresses on the patient's spine.

It is further an object of the invention to provide an artificial intervertebral disc that supports compression loads.

It is further an object of the invention to provide an artificial intervertebral disc that supports tension loads.

It is further an object of the invention to provide an artificial intervertebral disc that prevents lateral translation of the baseplates relative to one another.

It is further an object of the invention to provide an artificial intervertebral disc that provides a centroid of motion centrally located within the intervertebral space.

It is further an object of the invention to provide artificial intervetebral disc that provides maximized strength without increasing the height of the disc.

Other objects of the invention not explicitly stated will be set forth and will be more clearly understood in conjunction with the descriptions of the preferred embodiments disclosed hereafter.

SUMMARY OF THE INVENTION

The preceding objects are achieved by the invention, which is an artificial intervertebral disc or intervertebral spacer device, comprising a pair of support members (e.g., spaced apart baseplates), each with an outwardly facing surface.

Because the artificial disc is to be positioned between the facing endplates of adjacent vertebral bodies, the baseplates are arranged in a substantially parallel planar alignment (or slightly offset relative to one another in accordance with proper lordotic angulation) with the outwardly facing surfaces directed away from one another. The baseplates are to mate with the vertebral bodies so as to not rotate relative thereto, but rather to permit the spinal segments to bend or axially compress relative to one another in manners that mimic the natural motion of the spinal segment. This natural motion is permitted by the performance of a bearing disposed between the secured baseplates, and the securing of the baseplates to the vertebral bone is preferably achieved through the use of a vertebral body contact element attached to, or a surface feature of, the outwardly facing surface of each baseplate.

Preferable body contact elements include, but are not limited to, a convex mesh (of any shape or contour, but preferably domed) and one or more spikes. These vertebral body contact elements are disclosed in greater detail in application Ser. No. 10/256,160 ("the '160 Application") and application Ser. No. 10/642,258 ("the '258 Application"), which are incorporated herein by reference.

To enhance the securing of the baseplates to the vertebral bones, each baseplate preferably further comprises a surface feature that permits the long-term ingrowth of vertebral bone into the baseplates. A preferred surface feature is a porous area, which at least extends in a ring around the lateral rim of each outwardly facing surface. The porous area may be, for example, a sprayed deposition layer, an adhesive applied beaded metal layer, or another suitable porous coating known in the art. The porous ring permits the long-term ingrowth of vertebral bone into the baseplates, thus permanently securing the prosthesis within the intervertebral space.

The semispherical bearing disposed between the baseplates permits rotation and angulation of the two baseplates relative to one another and to the bearing, which establishes a centroid of motion (for this rotation and angulation) centrally between the baseplates. The semispherical bearing is captured between the baseplates by first and second retaining caps which are connected together by engagement of compression locking posts. Further, the capturing prevents separation and/or disassembly of the device under tension loading, and prevents lateral translation of the baseplates, during the rotation and angulation.

More specifically, the two baseplates of the present invention each include an aperture and each is secured to a bored central bearing in the following manner. The first and second baseplates are disposed such that their outwardly facing surfaces face away from one another, and their inwardly facing surfaces are directed toward one another. The second baseplate aperture is then passed over the compression locking post of second retaining cap and integral second retaining cap such that the compression locking post passes through the outwardly facing surface first and the inwardly facing surface second. A circumferential protrusion in the second baseplate aperture wall (i.e., the axially inwardly directed surface of the second baseplate) will rest upon the inwardly facing surface of the second retaining cap. Next, the bore of the central bearing is passed over the compression locking post and into the second baseplate aperture until a portion of the bearing having a smaller diameter contacts the inwardly facing surface of the second retaining cap and a portion of the bearing having a larger diameter contacts the inwardly facing surface of the circumferential protrusion in the wall of the second baseplate aperture. Then, the first baseplate aperture is passed over the compression locking post until the circumferential protrusion in the first baseplate aperture wall (i.e., the axially inwardly directed surface of the first baseplate) rests upon the bearing. Finally, compression locking post of the first retaining cap is pressed into the bearing bore and over the compression locking post of the second retaining cap under a force sufficient to compression lock the two compression locking posts, its integral retaining caps, and the bearing. At this point, the two retaining caps, compression locking posts, and bearing become one stationary unit (i.e., the retaining caps, compression locking posts, and bearing do not rotate or otherwise move relative to each other). The baseplates are free to rotate and articulate about the bearing and its firmly affixed retaining caps and post).

After assembly, as described above, the inwardly facing surfaces of the baseplate aperture walls (i.e., the surfaces extending from the circumferential protrusion in each aperture wall to the inward edge of each aperture wall) provide bearing surfaces, within which the bearing is captured, thereby facilitating limited angulation of the baseplates relative to the bearing. These bearing surfaces are preferably contoured to closely accommodate the spherical contour defined by the bearing, such that the bearing may easily contact and slide against the bearing surfaces. In this manner, the baseplate bearing surfaces, and therefore the baseplates, may angulate with limitation about the bearing.

As noted above, angulation of the baseplates relative to the bearing is limited. The outwardly facing surfaces of the baseplate aperture walls (i.e., the surfaces extending from the circumferential protrusion in each aperture wall to the outward edge of each aperture wall) are tapered to a larger diameter toward the baseplate's outwardly facing surfaces. Additionally, and preferably, the conformation of the taper matches the contour defined by the inwardly facing surface of the respective retaining cap. Because the retaining caps and posts are stationary with respect to the bearing, such tapering and conformation of the baseplate aperture wall permits the baseplates to angulate (about the centroid of motion at the center of the bearing) with respect to the bearing until the point at which the baseplate interferes with, or contacts, the respective retaining cap. Therefore, the taper, diameter, and conformation of this articulation (i.e., the space between the retaining cap and its respective baseplate) limit the angular movement of the respective baseplate relative to the bearing. Preferably, the taper, diameter, and conformation of the taper accommodate rotation of the respective baseplate relative to the bearing at least until the inwardly facing surfaces of the baseplates meet.

Furthermore, in the preferred embodiment of the present invention, the axial rotation of each baseplate is limited, preferably to between 7 and 10 degrees. This limitation may be created using a variety of methods. For example, this can be realized by a notch and groove, wherein notches are formed in each retaining cap and grooves are formed in each baseplate. Alternatively, the grooves may be formed in the retaining caps and the notches may be formed in the baseplates.

Accordingly, the baseplates rotate with limitation relative to the bearing. Because the bearing is secured to the baseplates with the compression locking posts and retaining caps as discussed above, the artificial intervertebral disc of the present invention can withstand tension loading of the baseplates, and the assembly does not come apart under normally experienced tension loads. Thus, in combination with the securing of the baseplates to the adjacent vertebral bones, the disc assembly has an integrity similar to the tension-bearing integrity of a healthy natural intervertebral disc. Also because the bearing is laterally captured between the bearing surfaces, lateral translation of the baseplates relative to one another is prevented during rotation and angulation, similar to the performance of a healthy natural intervertebral disc. The baseplates are designed to rotate relative to the bearing, therefore, the disc assembly provides a centroid of motion within the bearing. Accordingly, the centroid of motion of the disc assembly remains centrally located between the vertebral bodies, similar to the centroid of motion in a healthy natural intervertebral disc.

In addition to the features and functions described above for the baseplate apertures, the present invention can take advantage of the concavities of the adjacent vertebral bodies, and allow the size of the bearing, and accordingly its ability to withstand compression and tension loads, to be maximized. Specifically, the present invention is designed to allow each retaining cap to protrude beyond the outwardly facing surface of the respective baseplate into the concavity of the vertebral body adjacent to the outwardly facing surface, facilitating rotation of the baseplate on the bearing 28. Moreover, enlargement of the bearing creates a more robust bearing assembly that is able to withstand greater compression and tension forces than the same bearing assembly having a smaller size.

It should be understood that each of the features of the preferred and alternate embodiments described herein, including, but not limited to, formations and functions of baseplates, manners of contacting the bearing ball with bearing surfaces, manners of limiting rotation of the baseplates relative to one another, and manners of allowing the bearing mechanism to extend into the concavities of adjacent vertebral bodies, can be included in other embodiments, individually or with one or more of the other features, in other permutations of the features, including permutations that are not specifically described herein, without departing from the scope of the present invention.

BRIEF DESCRIPTION OF THE DRAWINGS

FIGS. 1f-1h show side cutaway perspective exploded (FIG. 1f) and side cutaway assembled perspective and straight (FIGS. 1g and 1h) views of the preferred embodiment of the present invention.

DETAILED DESCRIPTION

While the invention will be described more fully hereinafter with reference to the accompanying drawings, in which particular embodiments and methods of implantation are shown, it is to be understood at the outset that persons skilled in the art may modify the invention herein described while achieving the functions and results of the invention. Accordingly, the descriptions that follow are intended to be illustrative and exemplary of specific structures, aspects, and features within the broad scope of the invention and not as limiting of such broad scope.

Figure 1A:
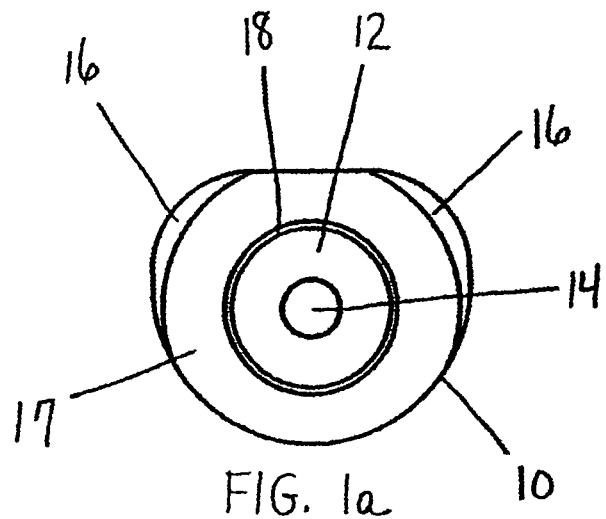
FIGS. 1a-c show top (FIG. 1a), side (FIG. 1b), and bottom (FIG. 1c) views of an assembled preferred embodiment of the present invention.
Figure 1B:
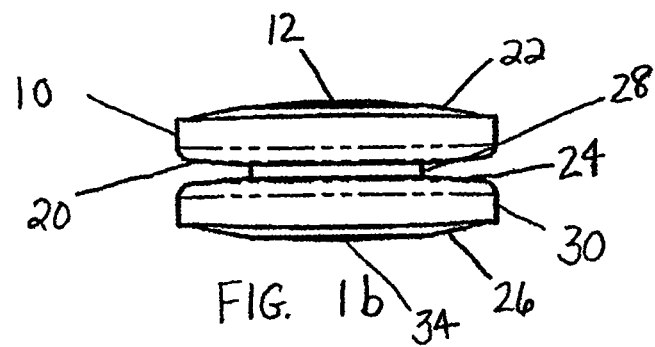
Figure 1C:
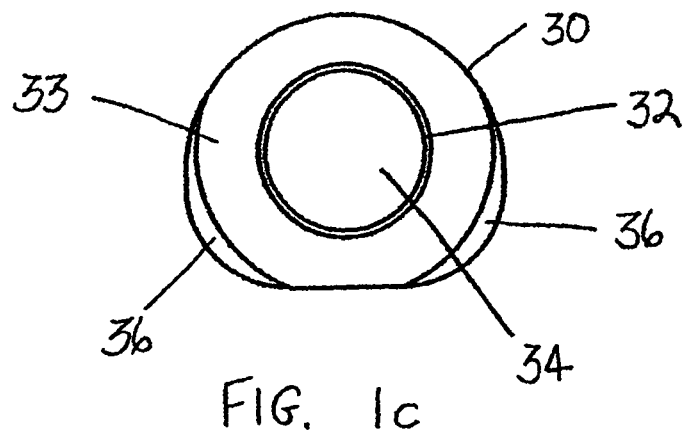
Figure 1E:
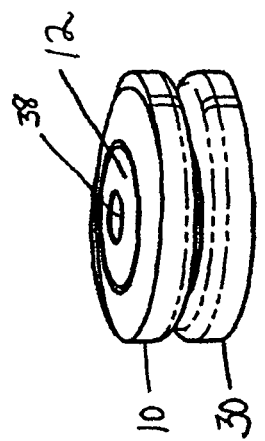
FIGS. 1d-1e show exploded (FIG. 1d) and assembled (FIG. 1e) views of the preferred embodiment of the present invention.
Figure 1D:
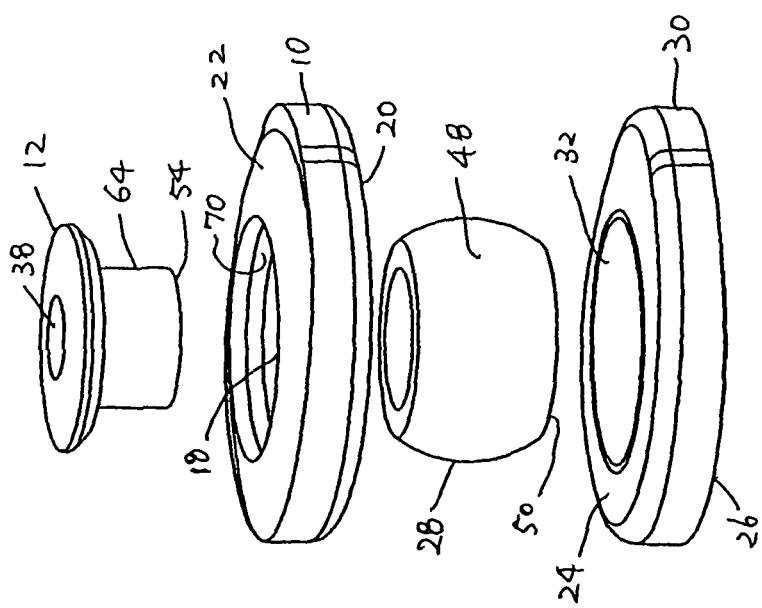
Figure 1F:
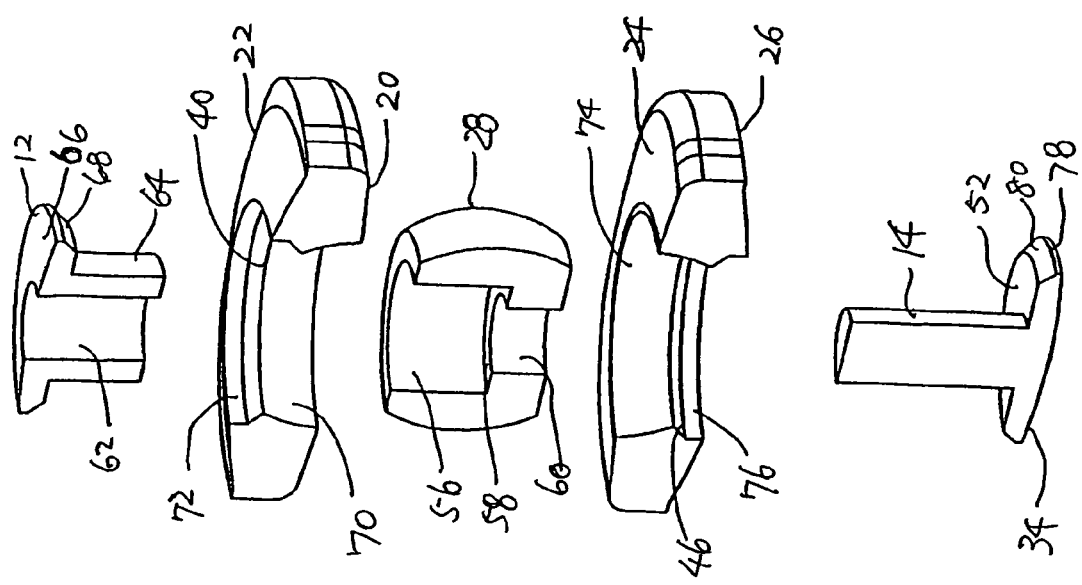
Figure 19:
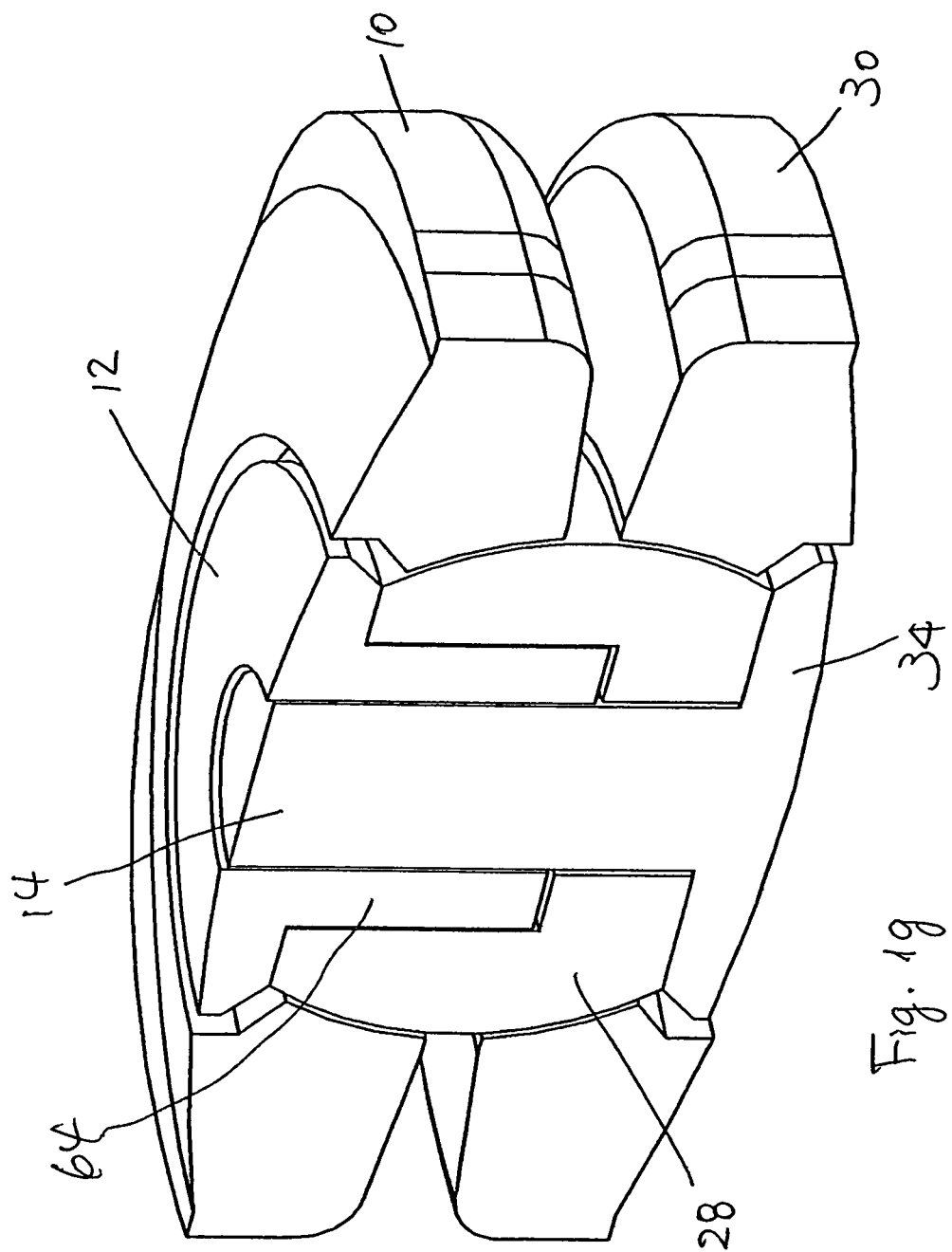
Figure 1H:
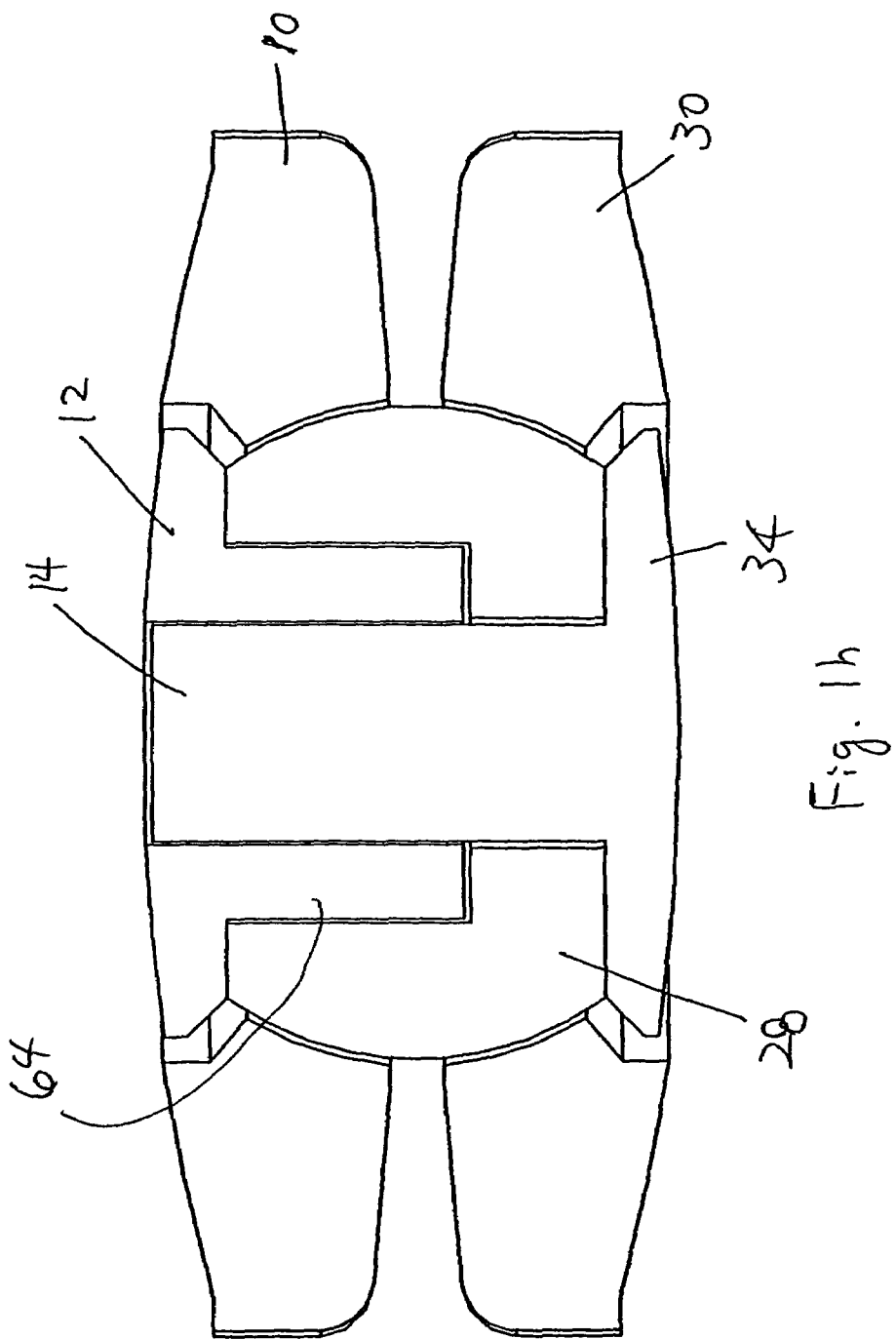
Figure 2:
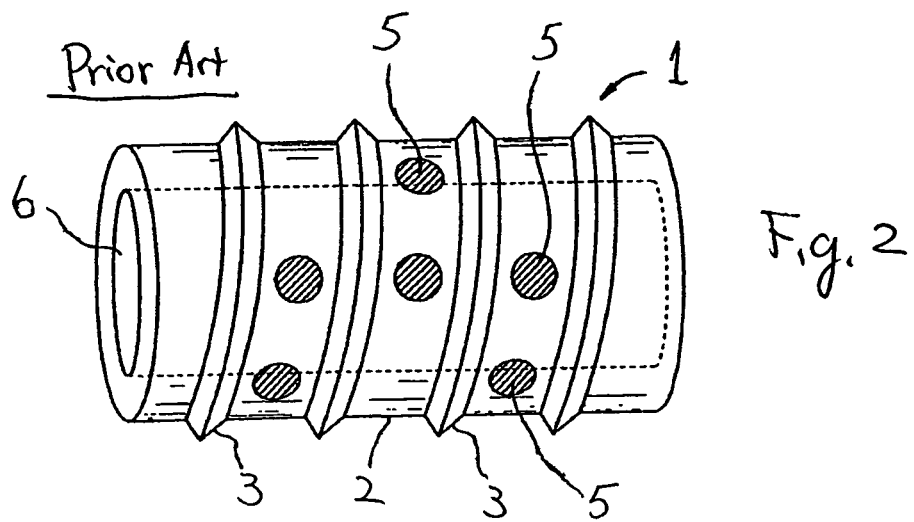
FIG. 2 shows a side perspective view of a prior art interbody fusion device.
Figure 3:
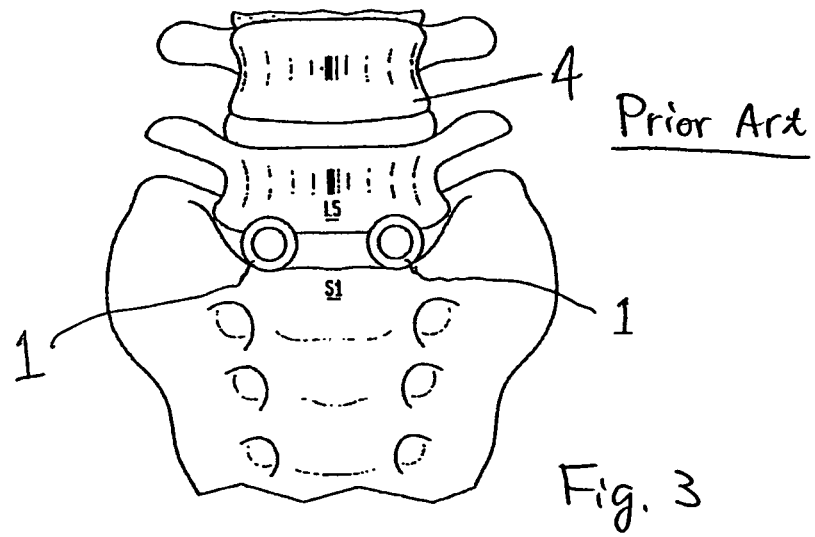
FIG. 3 shows a front view of the anterior portion of the lumbo-sacral region of a human spine, into which a pair of interbody fusion devices (as shown in FIG. 2) have been planted.

Referring first to FIGS. 1g and 1h, the artificial intervertebral disc assembly of the present invention generally comprises first and second endplates 10, 30 rotatably retained on a bearing 28 of a bearing mechanism which comprises bearing 28 and first and second retaining caps 12, 34. When assembled as shown in FIGS. 1g and 1h, retaining caps 12, 34 are connected to each other by engagement of respective compression locking posts 64, 14, whereby retaining caps 12, 34 and bearing 28 form an integrated piece and cannot move relative to one another, which will be explained in greater detail.

Referring also to FIGS. 1a-c, the assembled artificial intervertebral disc of the present invention is shown in top (FIG. 1a), side (FIG. 1b), and bottom (FIG. 1c) views. Generally, first baseplate 10 and second baseplate 30 rotate relative to bearing 28, which is captured between baseplates 10, 30 via first retaining cap 12 and second retaining cap 34. This capturing is accomplished by a compression locking post 14 of second retaining cap 34 and a compression locking post 64 of first retaining cap 12 compression locking to one another (via a bore 38 in compression locking post 64) and into axial bores 56, 60 in bearing 28 (See also FIGS. 1d-h.).

More specifically FIG. 1a depicts a top view of first baseplate 10, first retaining cap 12, compression locking post 14, first baseplate beveled edges 16, and first baseplate aperture 18 of the preferred embodiment of the present invention.

First baseplate 10, as well as second baseplate 30 (FIGS. 1b-c), are solid baseplates preferably comprised of a metal or metal alloy, such as a metal alloy including cobalt-chromium. However, baseplates 10, 30 may also be comprised of other types of metal or non-metal materials without departing from the scope of the present invention.

As shown in FIG. 1d, compression locking post 64 of first retaining cap 12 has a compression locking post aperture 38 (FIG. 1d) slightly smaller in diameter than the outer diameter of compression locking post 14. This dimensional difference allows compression locking post 14 to be attached to compression locking post 64 of first retaining cap 12 via a compression lock (i.e., forcing compression locking post 14 into compression locking post 64 of first retaining cap aperture 38 via application of pressure, such that the two cannot be separated absent a separation force greater than those experienced under spinal loads that can be survived by the patient). Alternatively or in addition to a compression locking attachment method, other methods of attaching compression locking post 14 to compression locking post 64 of first retaining cap 12 may be incorporated, including, but not limited to, laser welding (i.e., the laser weld may be applied from the outwardly facing surface of compression locking post 64 of first retaining cap 12 at the point where it contacts compression locking post 14), threading, etc. Thus, first and second retaining caps 12, 34 and bearing 28 sandwiched therebetween form an integrated piece and cannot move relative to one another. The integration of caps 12, 34 and bearing 28 can also be realized or enhanced by compression locking (or threading engagement, etc) between posts 14, 64 and bearing bores 60, 56.

Referring to FIGS. 1d and 1f, first baseplate 10 includes first baseplate outwardly facing surface 22 and first baseplate aperture 18. The aperture wall (i.e., the axially inwardly directed surface) of first baseplate 10 contains a first baseplate circumferential protrusion 40 (FIG. 1f) that retains first baseplate 10 between first retaining cap 12 and bearing 28 while allowing first baseplate 10 to rotate relative to bearing 28, as described in greater detail below with respect to FIG. 1f.

Referring next to FIG. 1b, shown is a side view of baseplates 10, 30 and bearing 28. Also depicted in FIG. 1b, first baseplate inwardly facing surface 20 is flat, and first baseplate outwardly facing surface 22 is shaped as a convex dome. Similarly, second baseplate inwardly facing surface 24 is flat, and second baseplate outwardly facing surface 26 is shaped as a convex dome. Although the outwardly facing surfaces 22, 26 of baseplates 10,30 of the preferred embodiment of the present invention are preferably shaped as convex domes so as to match the shape of the endplates of adjacent vertebral bodies to which the baseplates 10, 30 are to be attached, it should be noted that the outwardly facing surfaces of the baseplates are not limited to this particular shape. Also, as depicted, because clearance between retaining caps 12, 34 and baseplates 10, 30 allows rotation of the baseplate on the bearing 28, retaining caps 12, 34 may protrude slightly from baseplate outwardly facing surfaces 22, 26 during such rotation. After insertion of the device between vertebral bodies, retaining caps 12,34 protrude slightly into the concavities of vertebral bodies located adjacent to baseplates 10, 30, respectively.

Since the artificial disc of the present invention is to be positioned between the facing surfaces of adjacent vertebral bodies, baseplates 10, 30 of the present invention are disposed such that baseplate outwardly facing surfaces 22, 26 face away from one another as best illustrated in the assembly view in FIG. 1d. Baseplate outwardly facing surfaces 22, 26 include first baseplate beveled edges 16 (FIG. 1a) and second baseplate beveled edges 36 (FIG. 1c), respectively, and are designed to conform to the overall shape of the respective endplates of the vertebral bodies with which they will mate.

Preferably, baseplate outwardly facing perimeter regions 17,33 (FIG. 1a, c) of baseplate outwardly facing surfaces 22, 26 are osteoconductive due to, for example, a sprayed deposition layer, an adhesive applied beaded metal layer, or a similar suitable porous coating that is applied to these surfaces using methods known in the art. These baseplate outwardly facing surfaces 22, 26 permit the long-term ingrowth of vertebral bone into baseplates 10, 30, thus permanently securing the artificial intervertebral disc within the intervertebral space. The material applied to create the osteoconductive baseplate outwardly facing perimeter regions 17,33 of baseplate outwardly facing surfaces 22, 26 may extend closer to baseplate apertures 18, 32. However, it is most important that this osteoconductive material is applied to the portions of baseplate outwardly facing surfaces 22, 26 that seat directly against the adjacent vertebral body.

An alternate embodiment of the present invention may include one or more vertebral body contact elements including, but not limited to, a convex mesh, a convex dome, and one or more spikes as disclosed in the '160 and '258 Applications. These elements could be attached to baseplate outwardly facing surfaces 22, 26, also as described in the '160 and '258 Applications.

It should also be noted that depending upon the magnitude of expansion or contraction of the baseplates relative to each other, if any, first retaining cap 12 and second retaining cap 34, might protrude outward from the baseplate outwardly facing surfaces 22, 26, respectively. It should be further noted that the convex mesh, also disclosed in the '160 Application, is suitable for use with the present invention, and preferably should be attached to baseplate outwardly facing surfaces 22, 26, outside of the area of motion of retaining caps 12, 34. Such attachment may be performed via a variety of methods including, but not limited to, laser welding, or more preferably, plasma burying (i.e., the perimeter region of the convex mesh is buried under a plasma coating, which coating secures to the outwardly facing surface of the baseplate to which it is applied, and thus secures the convex mesh to the outwardly facing surface). Preferably, the convex mesh has a concavity such that contact with retaining caps 12,34 is avoided.

Baseplates 10, 30 are designed to mate with the vertebral bodies such that they do not rotate relative thereto, but rather permit the spinal segments to bend relative to one another in manners that mimic the natural motion of the spinal segment. This motion is permitted by the performance of bearing 28 disposed between baseplates 10, 30, which are secured thereto via compression locking posts 14, 64 (FIG. 1d), first retaining cap 12 (FIG. 1a), and second retaining cap 34 (FIG. 1c).

Baseplates 10, 30 are joined with bearing 28, first retaining cap 12, and second retaining cap 34. In a preferred embodiment of the present invention, bearing 28 has a semispherical shape, however, other shapes may be incorporated without departing from the scope of the present invention. Each of baseplates 10, 30 includes bearing surfaces 70, 74 (FIG. 1f), respectively, within which bearing 28 is capturable to allow limited rotation of baseplates 10, 30 relative to bearing 28. Each bearing surface is semispherically contoured to closely accommodate and engage with the spherical contour defined by bearing 28, such that baseplates 10, 30 may rotate transverse to the axis of the spine and may rotate relative to bearing 28 about a centroid of motion located at the center of bearing 28. As illustrated in FIG. 1f, bearing 28 includes first bearing bore 56, which accepts compression locking post 64 protruding from first retaining cap 12 (FIG. 1d), as well as second bearing bore 60, which accepts compression locking post 14 inserted into compression locking post aperture 38 of compression locking post 64. Preferably, compression locking post 64 locks into first bearing bore 56 via a compression lock. In the preferred embodiment of the present invention, the bearing bore comprises a first bearing bore 56 and a second bearing bore 60, each section having a different diameter, however, an alternate embodiment of the present invention may include a single bearing bore having a single, consistent diameter.

In the preferred embodiment of the present invention, the diameter of bearing 28 is slightly larger than the diameters of baseplate apertures 18, 32 (FIGS. 1a, 1c), such that during axial compression of baseplates 10, 30 and no, or minimal, angular rotation of either of baseplates 10, 30, baseplate bearing surfaces 70, 74 directly contact axially outwardly directed bearing surface 48, and baseplate inwardly facing surfaces 20, 24 do not make contact. Therefore, in an axially compressed state, baseplates 10, 30, and the vertebral bodies adjacent thereto, retain the ability to rotate relative to bearing 28. This allowed rotation mimics that found in the corresponding sections of a natural spine.

Referring next to FIG. 1c, shown are bottom views of second baseplate 30, second baseplate aperture 32, second baseplate outwardly facing perimeter region 33, second retaining cap 34, and second baseplate beveled edges 36. In the preferred embodiment of the present invention, second retaining cap 34 and compression locking post 14 (FIG. 1a) are manufactured as a single component. However, in an alternate embodiment of the present invention, second retaining cap 34 and compression locking post 14 are manufactured as separate components and are affixed to each other during assembly of the present invention. The methods of attachment include, but are not limited to, compression locking and threading.

Turning next to FIGS. 1d and 1e, shown are an exploded view (FIG. 1d) and an assembly view (FIG. 1e) of the preferred embodiment of the present invention. Assembly of the artificial intervertebral disc is as follows. Baseplates 10, 30 are disposed such that their baseplate outwardly facing surfaces 22, 26, respectively, face away from one another and their baseplate inwardly facing surfaces 20, 24, respectively, are directed toward one another. Second baseplate aperture 32 is then passed over compression locking post 14 and integral second retaining cap 34 such that compression locking post 14 passes through second baseplate outwardly facing surface 26 first and through second baseplate inwardly facing surface 24 second, and until the second retaining cap inwardly facing tapered surface 80 is in contact with tapered second baseplate outwardly facing aperture wall surface 76 (FIG. 1*f*) (i.e., the surface extending from second baseplate circumferential protrusion 46 (FIG. 1*f*) to the outward edge of the aperture wall). Next, second bearing bore 60 (FIG. 1*f*), and, consequently, first bearing bore 56 (FIG. 1*f*), are passed over compression locking post 14 until outwardly facing bearing surface 50 contacts inwardly facing second retaining cap surface 52 of second retaining cap 34 and axially outwardly directed bearing surface 48 contacts second baseplate bearing surface 74 (FIG. f). Then, first baseplate aperture 18 is passed over compression locking post 14 until first baseplate circumferential protrusion 40 (FIG. 1*f*) and first baseplate bearing surface 70 contact axially outwardly directed bearing surface 48. Finally, compression locking post 64 of first retaining cap 12 is passed over compression locking post 14 into first bearing bore 56 (FIG. 1*f*) under a force sufficient to radially compress compression locking post 14 and radially expand first bearing bore 56 (FIG. 1*f*). Force is applied until inwardly facing first retaining cap surface 54 is in contact with second bearing bore inwardly facing surface 58 (FIG. 1*f*) of second bearing bore 60 (FIG. 1*f*). After the force is removed, the radial pressure exerted by compression locking post 14 on first retaining cap axially inwardly directed surface (inner surface) 62 (FIG. 1*f*) of compression locking post 64 of first retaining cap 12, as well as the radial pressure exerted by compression locking post 64 on first bearing bore 56 (FIG. 1*f*), acts to lock first retaining cap 12, bearing 28, and second retaining cap 34, such that these components do not separate and do not rotate or, otherwise move, relative to each other.

Referring next to FIGS. 1*f*-1*h*, shown are a side cutaway exploded view (FIG. 1*f*) and a side cutaway assembly view (FIGS. 1*g* and 1*h*) of the preferred embodiment of the present invention. These side cutaway views depict the internal dimensions of each of the components of the present invention as well as the assembled configuration of each component relative to the other components.

As depicted in FIG. 1*f*, first retaining cap 12 comprises outward first retaining cap section 66, first retaining cap inwardly facing tapered surface 68, and compression locking post 64, which has a smaller diameter than outward first retaining cap section 66 [see above]. Similarly, first baseplate 10 has first baseplate circumferential protrusion 40, having the smallest diameter of any portion of first baseplate 10, and tapered first baseplate outwardly facing aperture wall surface 72, which is tapered to mate with first retaining cap inwardly facing tapered surface 68. Furthermore, first baseplate 10 has a first baseplate bearing surface 70 having a concavity equivalent, or near equivalent, to the contour defined by bearing 28.

Similarly, also as depicted in FIG. 1*f*, compression locking post 14 with integral second retaining cap 34 comprises outward second retaining cap section 78 and second retaining cap inwardly facing tapered surface 80. Second baseplate 30 has a second baseplate circumferential protrusion 46 having the smallest diameter of any portion of second baseplate 30, and tapered second baseplate outwardly facing aperture wall surface 76 tapered to mate with second retaining cap inwardly facing tapered surface 80. Furthermore, second baseplate 30 has a second baseplate bearing surface 74 having a concavity equivalent, or near equivalent, to the contour defined by bearing 28.

Accordingly, due to these configurations, the baseplates 10, 30 are able to rotate relative to bearing 28. The semispherical contour of first baseplate bearing surface 70 closely matches the spherical contour defined by bearing 28, such that first baseplate 10 can rotate about the centroid of motion located at the center of bearing 28. Further, tapered first baseplate outwardly facing aperture wall surface 72 is tapered to a larger diameter toward the first baseplate outwardly facing surface 22. Additionally, and preferably, the conformation of the taper matches the contour defined by first retaining cap inwardly facing tapered surface 68. Since first retaining cap 12 and compression locking post 64 are stationary with respect to bearing 28, such tapering and conformation of tapered first baseplate outwardly facing aperture wall surface 72 permits first baseplate 10 to rotate (about the centroid of motion at the center of bearing 28) with respect to bearing 28 until the point at which first baseplate 10 interferes with, or contacts, the first retaining cap inwardly facing tapered surface 68. Therefore, the taper, diameter, and conformation of these interacting elements (i.e., the formation of the space between first retaining cap 12 and first baseplate 10) can be established to limit the rotational ability of the first baseplate 10 relative to bearing 28. Preferably, the taper, diameter, and conformation of these interacting elements accommodate rotation of first baseplate 10 relative to bearing 28 at least until baseplate inwardly facing surfaces 20, 24 of baseplates 10, 30 meet. In other words, the ability of first baseplate 10 to rotate relative to bearing 28 is limited by the distance between first retaining cap inwardly facing tapered surface 68 and first baseplate 10, as well as the distance between baseplates 10, 30.

Similarly, the semispherical contour of second baseplate bearing surface 74 closely matches the spherical contour defined by bearing 28, such that bearing 28 can rotate about the about a centroid of motion located at the center of bearing 28. Further, tapered second baseplate outwardly facing aperture wall surface 76 is tapered to a larger diameter toward the second baseplate outwardly facing surface 26. Additionally, and preferably, the conformation of the taper matches the contour defined by second retaining cap inwardly facing tapered surface 80. Since second retaining cap 34 and compression locking post 14 are stationary with respect to bearing 28, such tapering and conformation of tapered second baseplate outwardly facing aperture wall surface 76 permits second baseplate 30 to rotate (about the centroid of motion at the center of bearing 28) with respect to bearing 28 until the point at which second baseplate 30 interferes with, or contacts, the second retaining cap inwardly facing tapered surface 80. Therefore, the taper, diameter, and conformation of these interacting elements (i.e., the formation of the space between second retaining cap 34 and second baseplate 30) can be established to limit the rotational ability of the second baseplate 30 relative to bearing 28. Preferably, the taper, diameter, and conformation of these interacting elements accommodate rotation of second baseplate 30 relative to bearing 28 at least until baseplate inwardly facing surfaces 20, 24 of baseplates 10, 30 meet. In other words, the ability of second baseplate 30 to rotate relative to bearing 28 is limited by the distance between second retaining cap inwardly facing tapered surface 80 and second baseplate 30, as well as the distance between baseplates 10, 30.

In the preferred embodiment of the present invention, the axial rotation of baseplates 10, 30 (about the longitudinal axis of the spine) is unlimited. In other embodiments, the axial rotation is limited, preferably to from 7 to 10 degrees. This limitation may be created using a variety of methods including, for example, a notch formed in retaining caps 12, 34 and a groove formed in baseplates 10, 30. Alternatively, the groove may be formed in retaining caps 12,34 and the notch may be formed in baseplates 10, 30.

As best shown in FIGS. g and 1h, clearance exists between the baseplates 10, 30 and the bearing 28, as well as between the baseplates 10, 30 and the retaining caps 12, 34, whereby the baseplates 10, 30 are not only capable of rotating and angulating about the centroid of motion at the center of the bearing 28, but also capable of floating along the axial direction relative to each other, thus realizing a universal motion of the baseplates. When the baseplates float toward each other, the retaining caps 12 and 34 may protrude slightly beyond the outwardly facing surfaces of the baseplates 10, 30, and are accepted by the spaces formed by the concave contour of the endplates of the vertebral bodies.

The diameter of bearing 28, and its corresponding ability to withstand compression and tension stress loads, can be increased without a need to increase the height of the bearing 28 (which is limited by the spacing between adjacent vertebral bodies). Increasing the diameter of bearing 28 also increases the bearing surface and reduces point loading. Consequently, a more robust artificial intervertebral disc is achieved that is capable of withstanding the naturally occurring compression and tension forces exerted by adjacent vertebral bodies.

Whereas specific embodiments of an artificial intervertebral disc have been described and illustrated herein, it will be apparent to those of skill in the art that variations and modifications to that disclosed herein are possible without deviating from the broad spirit, scope, and principles of the present invention. Therefore, the present invention shall not be limited to the specific embodiments disclosed herein.

The invention claimed is:

1. A method of assembling an artificial intervertebral disc comprising:
   inserting a first locking post of a first retaining cap through a first baseplate aperture in a first baseplate and at least partially through a first bearing bore in a bearing; and
   inserting a second locking post of a second retaining cap through a second baseplate aperture in a second baseplate and at least partially through a second bearing bore in the bearing, the first and second bearing bores each having a different diameter,
   wherein the first and second locking posts engage with one another and the first and second baseplates are rotatably retained on the bearing, such that the first and second baseplates and the bearing are configured to rotate relative to one another after implantation of the artificial intervertebral disc into a patient,
   and wherein each of the first and second retaining caps has a flange.

2. The method of claim 1, further comprising a step of mating the first locking post with the second locking post.

3. The method of claim 2, wherein the mating step includes inserting the second locking post into a first retaining cap aperture of the first retaining cap.

4. The method of claim 3, wherein the first retaining cap aperture extends at least partially through the first locking post.

5. The method of claim 3, wherein the mating step includes compression locking the second locking post within the first retaining cap aperture.

6. The method of claim 3, wherein the mating step includes laser welding the second locking post within the first retaining cap aperture.

7. The method of claim 1, further comprising steps of capturing the bearing within a first bearing surface formed on the first baseplate and capturing the bearing within a second bearing surface formed on the second baseplate.

8. The method of claim 1, further comprising steps of arranging a first inwardly facing surface of the first baseplate and a second inwardly facing surface of the second baseplate so that they face one another and arranging a first outwardly facing surface of the first baseplate and a second outwardly facing surface of the second baseplate so that they face away from one another.

9. The method of claim 8, wherein the inserting steps include placing a first retaining cap section of the first retaining cap adjacent the first outwardly facing surface and placing a second retaining cap section of the second retaining cap adjacent the second outwardly facing surface.

10. The method of claim 1, further comprising steps of contacting the bearing with a first circumferential protrusion of the first baseplate and a second circumferential protrusion of the second baseplate.

11. The method of claim 1, wherein the inserting steps include inserting the first locking post completely through the first bearing bore formed in the bearing and inserting the second locking post completely through the second bearing bore formed in the bearing.

12. The method of claim 1, further comprising a step of rotating the first baseplate with respect to the bearing.

13. The method of claim 12, further comprising a step of rotating the second baseplate with respect to the bearing.

14. A method of assembling an artificial intervertebral disc comprising:
   inserting a first locking post of a first retaining cap through a first baseplate aperture in a first baseplate and at least partially through a bearing bore in a bearing; and
   inserting a second locking post of a second retaining cap through a second baseplate aperture in a second baseplate, at least partially through the bearing bore, and into a first retaining cap aperture, the first retaining cap aperture extending completely through the first retaining cap,
   wherein the first and second baseplates are rotatably retained on the bearing, such that the first and second baseplates and the bearing are configured to rotate relative to one another after implantation of the artificial intervertebral disc into a patient,
   and wherein each of the first and second retaining caps has a flange.

15. The method of claim 14, further comprising a step of compression locking the second locking post within the first retaining cap aperture.

16. The method of claim 14, further comprising a step of laser welding the second locking post within the first retaining cap aperture.

17. The method of claim 14, further comprising steps of capturing the bearing within a first bearing surface formed on the first baseplate and capturing the bearing within a second bearing surface formed on the second baseplate.

18. The method of claim 14, further comprising steps of arranging a first inwardly facing surface of the first baseplate and a second inwardly facing surface of the second baseplate so that they face one another and arranging a first outwardly facing surface of the first baseplate and a second outwardly facing surface of the second baseplate so that they face away from one another.

19. The method of claim 18, wherein the inserting steps include placing a first retaining cap section of the first retaining cap adjacent the first outwardly facing surface and placing a second retaining cap section of the second retaining cap adjacent the second outwardly facing surface.

20. The method of claim 14, further comprising steps of contacting the bearing with a first circumferential protrusion of the first baseplate and a second circumferential protrusion of the second baseplate.

21. The method of claim 14, wherein the inserting steps include inserting the first locking post into a first bearing bore formed in the bearing and inserting the second locking post into a second bearing bore formed in the bearing.

22. The method of claim 14, further comprising a step of rotating the first baseplate with respect to the bearing.

23. The method of claim 22, further comprising a step of rotating the second baseplate with respect to the bearing.

24. A method of assembling an artificial intervertebral disc comprising:
    inserting a first locking post of a first retaining cap through a first baseplate aperture in a first baseplate and at least partially through a first bearing bore in a bearing;
    inserting a second locking post of a second retaining cap through a second baseplate aperture in a second baseplate, at least partially through a second bearing bore in the bearing, and into a first retaining cap aperture of the first retaining cap; and
    compression locking the second locking post within the first retaining cap aperture,
    wherein the first and second baseplates are rotatably retained on the bearing, such that the first and second baseplates and the bearing are configured to rotate relative to one another after implantation of the artificial intervertebral disc into a patient,
    and wherein each of the first and second retaining caps has a flange, each of the flanges having a diameter that is greater than a diameter of the first and second bearing bores.

25. The method of claim 24, further comprising steps of arranging a first inwardly facing surface of the first baseplate and a second inwardly facing surface of the second baseplate so that they face one another and arranging a first outwardly facing surface of the first baseplate and a second outwardly facing surface of the second baseplate so that they face away from one another,
    wherein the inserting steps include placing a first retaining cap section of the first retaining cap adjacent the first outwardly facing surface and placing a second retaining cap section of the second retaining cap adjacent the second outwardly facing surface.

* * * * *